United States Patent
Nutting

[11] Patent Number: 5,547,381
[45] Date of Patent: Aug. 20, 1996

[54] FANGS AND APPLICATION THEREOF

[76] Inventor: Donald W. Nutting, 1295 Ithaca Dr., Boulder, Colo. 80303

[21] Appl. No.: 216,066

[22] Filed: Mar. 22, 1994

[51] Int. Cl.$^6$ ..................................................... A61C 5/08
[52] U.S. Cl. ............................................ 433/219; 433/180
[58] Field of Search ........................... 433/167, 168.1, 433/180, 183, 202.1, 218, 219, 171; 472/133, 70

[56]         References Cited

U.S. PATENT DOCUMENTS

| | | | |
|---|---|---|---|
| 1,379,063 | 5/1921 | Van Allen | 433/218 |
| 3,793,728 | 2/1974 | Corbineau | 433/183 |
| 4,015,332 | 4/1977 | Manne | 433/219 |
| 4,206,545 | 6/1980 | Lard | 433/188 |
| 4,430,061 | 2/1984 | Webb et al. | 433/9 |
| 4,678,435 | 7/1987 | Long | 433/218 |
| 4,738,622 | 4/1988 | Kawahara et al. | 433/180 |
| 5,102,337 | 4/1992 | Soroca | 433/178 |

FOREIGN PATENT DOCUMENTS 9103210   3/1991   WIPO ..................... 433/219

*Primary Examiner*—Cary E. O'Connor
*Attorney, Agent, or Firm*—James R. Young; Scott B. Allison; Chrisman, Bynum & Johnson

[57]            ABSTRACT

An artificial and removable tooth cap body and a method of easily attaching the tooth cap body to a real tooth. The tooth cap body is anchored to the real tooth with a low melting point and malleable thermoplastic material. The tooth cap body includes ridges and/or depressions so that the thermoplastic material can anchor and attach to the tooth cap body.

15 Claims, 1 Drawing Sheet

FANGS AND APPLICATION THEREOF

BACKGROUND OF THE INVENTION

1. Field of the Invention

This invention relates to a tooth cap body and a method of applying the tooth cap body to a person's real teeth.

2. Description of the Prior Art

In the course of parties, particularly Halloween parties, it is common to have people masquerade as vampires and other wild beasts. In doing so, these people are faced with the problem of using tooth cap bodies that simulate fangs. Traditionally, unless the tooth cap body is made by a dentist and/or the tooth cap body is cast for the specific person wearing it, there is always the problem of the tooth cap body falling out, causing the masquerader the embarrassment of losing virility as to the character he or she is performing.

SUMMARY OF THE INVENTION

A general object of this invention is to have a superior method of attaching a tooth cap body to a masquerader's tooth so that the tooth cap body does not fall out prematurely.

Another general object of this invention is to provide the ability to attach a tooth cap body to a real tooth without the need for specialized equipment or specialized training.

Another general object of this invention is to have a tooth cap body that is securely anchorable to a wearer's tooth.

Additional objects, advantages, and novel features of the invention shall be set forth in part in the description that follows, and in part will become apparent to those skilled in the art upon examination of the following or may be learned by the practice of the invention. The objects and the advantages may be realized and attained by means of the instrumentalities and in combinations particularly pointed out in the appended claims.

To achieve the foregoing and other objects and in accordance with the purposes of the present invention, as embodied and broadly described herein, the present invention includes a tooth cap body having ridges and/or depressions that can be anchored to a real tooth.

To further achieve the foregoing and other objects, the present invention further comprises a method of anchoring a tooth cap body to a real tooth, by placing a first portion of an initially malleable, but also hardenable material into a cavity in the tooth cap body and allowing another portion of the malleable material to extend from the first portion to outside the cavity, positioning the tooth cap body with the malleable material onto a real tooth in such a manner that the real tooth extends into the cavity and displaces some of the first portion of the malleable material and causing the first portion of the malleable material conform to surfaces of the real tooth that extend into the cavity, stretching the second portion of the malleable material around surface contours of adjacent teeth, and allowing the material to harden and thereby become anchored to the tooth cap body.

BRIEF DESCRIPTION OF THE DRAWINGS

The accompanying drawings, which are incorporated in and form a part of the specification, illustrate the preferred embodiments of the present invention, and together with the descriptions serve to explain the principles of the invention.

In the Drawings.

DETAILED DESCRIPTION OF THE PREFERRED EMBODIMENTS

Figure 1:
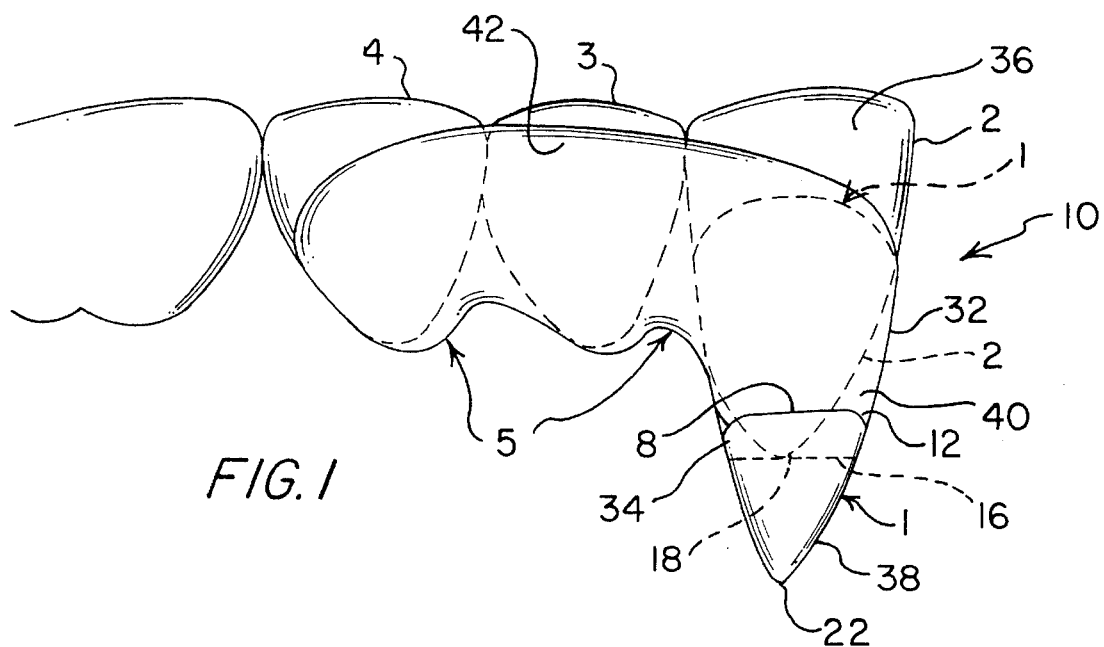
FIG. 1 is a view of the tooth cap apparatus mounted on the left upper canine tooth and anchored on the first and second upper left premolars looking from the inside of a wearer's mouth to the outside. The tooth cap body is positioned on the canine tooth and a portion of thermoplastic material extends from a cavity inside the tooth cap body to the first and second premolars.

In general, the method of attaching an artificial fang or tooth cap body 1 to a real tooth 2 uses a low melting point liquid thermoplastic material 5 to anchor the tooth cap body 1 to the surrounding teeth 3,4 and the tooth 2 being capped. The melted malleable thermoplastic material 5 is placed into the cavity 11 of the tooth cap body 1, and before the thermoplastic material 5 hardens, the thermoplastic material 5 is stretched by the masquerader across one or more surrounding teeth 3,4, and pressed and shaped around the contours of the surrounding teeth 3,4, so that the thermoplastic material 5 forms a solid anchor from the tooth cap body 1 to the surrounding teeth 3,4 after the thermoplastic material 5 hardens. Also, before the thermoplastic material 5 hardens, the masquerader bites into the thermoplastic material 5 repeatedly to custom fit the thermoplastic material 5 to his or her individual bite. After this procedure, the thermoplastic material 5 and the tooth cap apparatus 10 are formed and shaped to fit securely in the masquerader's mouth, and the masquerader can eat, drink, and talk without any fear that the tooth cap apparatus 10 will fall out. However, the masquerader can carefully pull the tooth cap apparatus 10 from his or her teeth 2, 3, 4 and re-use the tooth cap apparatus 10 many times over. The tooth cap apparatus 10 attaches by anchoring to the teeth 2, 3, 4 rather than by adhesion, so that no adhesives are necessary. Since no adhesives are required or used, the moth cap apparatus 10 is not bonded to the teeth 2, 3, 4, thereby allowing the tooth cap apparatus 10 to be removed from the masquerader's teeth 2, 3, 4.

The tooth cap body 1, the tooth cap apparatus 10 and the method of attaching the tooth cap body 1 to the real teeth 2, 3, 4, will now be discussed in more detail.

The real tooth 2 upon which the tooth cap body 1 will be positioned can be, for example, a canine tooth, a pre-molar tooth, a molar tooth, or an incisor tooth. The tooth cap body 1 includes a front side 32 and a back side 34. The tooth cap body 1 further includes an inside surface 12 and an outside surface 20 which converge to form an extension 38, a tip 22, and a trough 16. The inside surface 12 has a cavity 11 that extends toward the outside surface 20 from a peripheral rim 30 that substantially surrounds the cavity 11 and forms the front side 32 and the back side 34.

The tooth cap body 1 has an appropriate width W, size, and shape to conform to the lateral side 36 of the real tooth 2 so that when the tooth cap body 1 is placed on the real tooth 2, the tooth cap body 1 becomes a realistic and naturally appearing extension of the real tooth 2. The outside surface 20 has a convex shape to further accentuate the realistic visual effect of the tooth cap apparatus 10 for the masquerader, as well as to provide sufficient thickness to accommodate the cavity 11 extending therein from the inside, as described above and shown in FIG. 2.

The cavity 11 of the tooth cap body 1 includes varying surface features such as ridge(s) 6 and/or depression(s) 7. The liquid thermoplastic material 5 surrounds, fills in, and envelopes the ridges 6 and/or the depressions 7 when the tooth cap body I is positioned on the tooth 2 so that the thermoplastic material 5 firmly anchors and attaches itself to the tooth cap body 1 after the thermoplastic material 5 hardens, as will be discussed in more detail below.

Figures 2, 3:
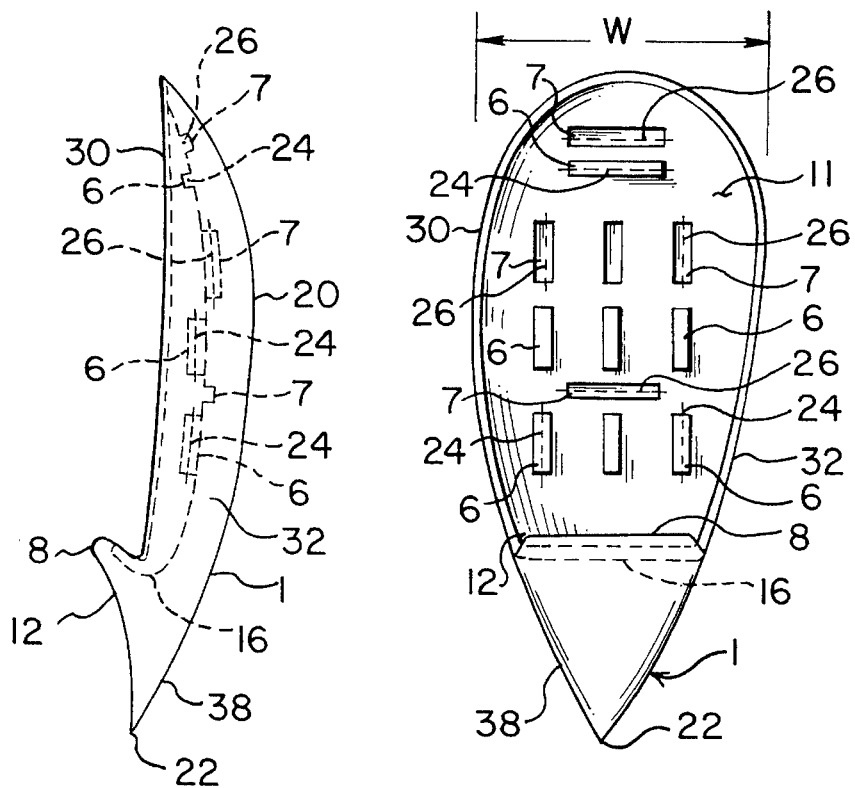
FIG. 2 is a front elevation view of the tooth cap body, showing the cavity as well as internal depressions and ridges in the cavity of the tooth cap body in phantom lines.
FIG. 3 is an elevation view of the inside of the tooth cap body showing the cavity as well as the internal depressions and ridges of the tooth cap body of this invention.

The ridges 6 and the depressions can be oriented either vertically, horizontally, or both, as best seen in FIG. 3. Furthermore, the outer rim 30 extends around the perimeter of the cavity 11. The ridge 6 and the depressions 7 need not have equal size or shape, as also illustrated in FIGS. 2 and 3. Each ridge 6, as best seen in FIG. 3, can have a longitudinal center axis 24, and each depression 7 can have a longitudinal center axis 26.

The method of attaching the tooth cap body 1 to the real tooth 2 is very easy and does not require specialized training or equipment.

Now referring to FIG. 1, a dob or first portion 40 of malleable, but eventually hardenable material 5, such as a low melting point thermoplastic material 5, is placed in the cavity 11 of the tooth cap body 1, substantially filling the cavity, while a second portion 42 of the material 5 extends outside the cavity 11. The tooth cap body 1 containing the thermoplastic material 5 in its cavity 11 can then be positioned with the canine tooth 2 extending into and displacing some of the material 5 from the cavity 11. The excess second portion 42 of the thermoplastic material 5 that extends outside the cavity 11 can then be stretched, shaped, and molded by the masquerader over the first premolar 3 and the second premolar 4, as shown in FIG. 1, thereby providing a strong anchor of the tooth cap body 1 onto the first 3 and second 4 premolar by means of the thermoplastic material 5.

Now referring to FIGS. 2 and 3, the combination of the ridges 6 and the depressions 7 in the cavity 11 of the tooth cap body 1 provide the tooth cap body 1 with structures to which the thermoplastic material 5 can become anchored to the tooth cap body 1. Anchoring the thermoplastic material 5 securely to the tooth cap body 1, for example with such ridges 6 and depressions 7 is preferred since the thermoplastic material 5 is not adhesively bonded to the tooth cap body 1. The ridges 6 and the depressions 7 prevent the thermoplastic material 5 from sliding or slipping in the tooth cap body 1 after the thermoplastic material 5 has hardened. More specifically, the ridges 6 and the depressions 7 restrict movement of the tooth cap body 1 relative to the thermoplastic material 5, and vice versa, even though the thermoplastic material 5 is not adhesively bonded to the tooth cap body 1. The combination provides a great amount of strength of attachment for the tooth cap apparatus 10 to the teeth 2, 3, 4.

When the tooth cap apparatus 10 is worn by the masquerader, the extremity edge 18 of the real tooth 2 is preferably positioned in the trough 16 of the tooth cap body 1 that is formed by a laterally inward and upward extension or lip 8. The lip 8 and the trough 16 of the tooth cap body 1 coact with the real tooth 2, as shown in FIG. 1, and further restrict or eliminate motion of the tooth cap body 1 relative to the real tooth 2 so that the tooth cap apparatus 10 remains securely anchored to the teeth 2, 3, 4 until the masquerader intentionally removes the tooth cap apparatus 10 from his or her mouth.

These ridge(s) 6 and/or depression(s) 7 play an even more important role when the inside surface 12 of the tooth cap body 1 is reduced to the lip 8 to facilitate the masquerader having a good bite so that the masquerader's lower teeth can mesh with the upper teeth as they normally do without interference of the inside surface 12 of the tooth cap body 1. When the tooth cap body 1 is reduced to a lip 8 on the inside surface 12 of the tooth cap body 1, there is little anchoring of the tooth cap body 1 to the thermoplastic material 5 from the inside surface 12, so the ridge(s) 6 and/or depression(s) 7 do the primary anchoring of the tooth cap body 1 to the thermoplastic material 5.

The foregoing description is considered as illustrative only of the principles of the invention. Furthermore, since numerous modifications and changes will readily occur to those skilled in the art, it is not desired to limit the invention to the exact construction and process shown and described above. Accordingly, all suitable modifications and equivalents may be resorted to falling within the scope of the invention as defined by the claims which follow.

What is claimed is:

1. Tooth extension apparatus for extending a person's real tooth in length to have the appearance of an animal fang, comprising:

a tooth cap body that has an outside surface, an inside surface, a front side, and a back side, said outside surface having a smoothly curved convex shape and said inside surface having a cavity extending therein toward said outside surface from a peripheral rim that substantially surrounds said cavity and forms said front side and said back side, said cavity conforming in size and shape to a lateral side of said real tooth and adapted to receive said lateral side of said real tooth when said tooth cap body is juxtaposed to said real tooth, said tooth cap body also having an extension that protrudes downwardly below said cavity and converging to a tip, and a lip protruding from said inside surface under said cavity to form a trough at the bottom of said cavity and adapted for receiving and retaining an extremity edge of the person's real tooth when said tooth cap body is juxtaposed to said real tooth and said lateral side of said real tooth is received in said cavity; and an initially malleable, but hardenable material of a quantity that is more than enough to fill said cavity, a first portion of said material being placed in said cavity and adapted to be partially displaced by said lateral side of said real tooth when said lateral side of said real tooth is received in said cavity, and a second portion of said material extending from said first portion out of said cavity to a sufficient extent to be formable around additional teeth that are adjacent said person's real tooth.

2. The tooth extension apparatus of claim 1, wherein said initially malleable but hardenable material is a thermal setting plastic material.

3. The tooth extension apparatus of claim 1, wherein said tooth cap body has a ridge that extends into said cavity.

4. The tooth extension apparatus of claim 1, wherein said tooth cap body has a depression that extends inwardly from said cavity toward said outside surface.

5. A method of extending a person's real tooth to have the appearance of an animal fang, comprising the steps of:

positioning a first portion of an initially malleable, but hardenable material in a cavity in a tooth cap that conforms in size and shape to the lateral side of the person's real tooth and that extends downwardly below the cavity to a tip and has a lip that protrudes inwardly and upwardly from the bottom of the cavity to form a trough;

extending a second portion of the initially malleable but hardenable material from said first portion outside said cavity;

juxtaposing said tooth cap with the person's real tooth in such a manner that the lateral side of the person's real tooth is received into said cavity and displaces some of said first portion of the initially malleable, but hardenable material and such that an extremity edge of the person's real tooth seats in said trough;

forming said second portion of said initially malleable, but hardenable material around other ones of the person's teeth adjacent the person's real tooth that is being extended; and hardening said initially malleable, but hardenable material.

6. A method of anchoring a tooth cap to a real tooth, comprising the steps of:

providing a tooth cap having a cavity with surface features;

placing an amount of malleable material into said cavity of said tooth cap;

positioning said tooth cap onto said real tooth so that said malleable material is forced to envelop said surface features in said cavity;

shaping any excess of said malleable material that is forced out of said tooth cap when said tooth cap is positioned onto said real tooth to conform said malleable material to teeth adjacent said real tooth; and allowing said malleable material to harden so that said malleable material is securely anchored to said tooth cap.

7. The method of claim 6, wherein said malleable material comprises a low melting point thermoplastic.

8. The method of claim 6, wherein said surface features include at least one ridge.

9. The method of claim 8, wherein said surface features include a plurality of ridges.

10. The method of claim 6, wherein said surface features include at least one depression.

11. The method of claim 10, wherein said surface features include a plurality of depressions.

12. The method of claim 10, wherein said surface features further include at least one ridge.

13. The method of claim 6, wherein said tooth cap includes a trough and a lip, and said tooth cap is positioned onto said real tooth such that said real tooth extends into said trough of said tooth cap.

14. The method of claim 13, wherein said real tooth engages said lip of said tooth cap when said tooth cap is positioned onto said real tooth.

15. The method of claim 6, including the step of biting into the malleable material after the tooth cap containing the malleable material is placed on the real tooth.

* * * * *

US005547381B1

REEXAMINATION CERTIFICATE (3868th)

United States Patent [19]
Nutting

[11] B1 5,547,381
[45] Certificate Issued Sep. 7, 1999

[54] FANGS AND APPLICATION THEREOF

[76] Inventor: Donald W. Nutting, 1295 Ithaca Dr., Boulder, Colo. 80303

Reexamination Request:
No. 90/005,156, Oct. 23, 1998

Reexamination Certificate for:
Patent No.: 5,547,381
Issued: Aug. 20, 1996
Appl. No.: 08/216,066
Filed: Mar. 22, 1994

[51] Int. Cl.⁶ ................................................ A61C 5/08
[52] U.S. Cl. ........................................ 433/219; 433/180
[58] Field of Search .............................. 433/167, 168.1, 433/180, 183, 171, 202.1, 218, 219; 472/70, 133

[56] References Cited

U.S. PATENT DOCUMENTS

| | | | |
|---|---|---|---|
| 1,379,063 | 5/1921 | Van Allen | 433/218 |
| 2,057,341 | 10/1936 | Morgan | 433/168.1 |
| 3,558,540 | 1/1971 | Molnar | 260/23 |
| 3,793,728 | 2/1974 | Corbineau | 433/183 |
| 4,015,332 | 4/1977 | Manne | 433/219 |
| 4,206,545 | 6/1980 | Lard | 433/188 |
| 4,251,215 | 2/1981 | May et al. | 433/168 |
| 4,361,528 | 11/1982 | Ginsburg et al. | 264/28 |
| 4,430,061 | 2/1984 | Webb et al. | 433/9 |
| 4,678,435 | 7/1987 | Long | 433/218 |
| 4,738,622 | 4/1988 | Kawahara et al. | 433/180 |
| 5,102,337 | 4/1992 | Soroca | 433/178 |

FOREIGN PATENT DOCUMENTS 9103210  3/1991  WIPO .................................. 433/219

OTHER PUBLICATIONS

"Fangtastic's " fang instruction sheet and example photographs.
"Generik Ink, Inc. Why Not Party? Custom Fangs", copyright 1989.
"Generik Ink, Inc. Why Not Party? Blood and Fangs" advertisement.
"Generik Ink, Inc., Why Not Party?®Horror Film™ Make–Up" instruction sheet, copyright 1988.
"Friendly Plastic® Modeling Material" instruction sheet, copyright 1986.

*Primary Examiner*—John J. Wilson

[57] ABSTRACT

An artificial and removable tooth cap body and a method of easily attaching the tooth cap body to a real tooth. The tooth cap body is anchored to the real tooth with a low melting point and malleable thermoplastic material. The tooth cap body includes ridges and/or depressions so that the thermoplastic material can anchor and attach to the tooth cap body.

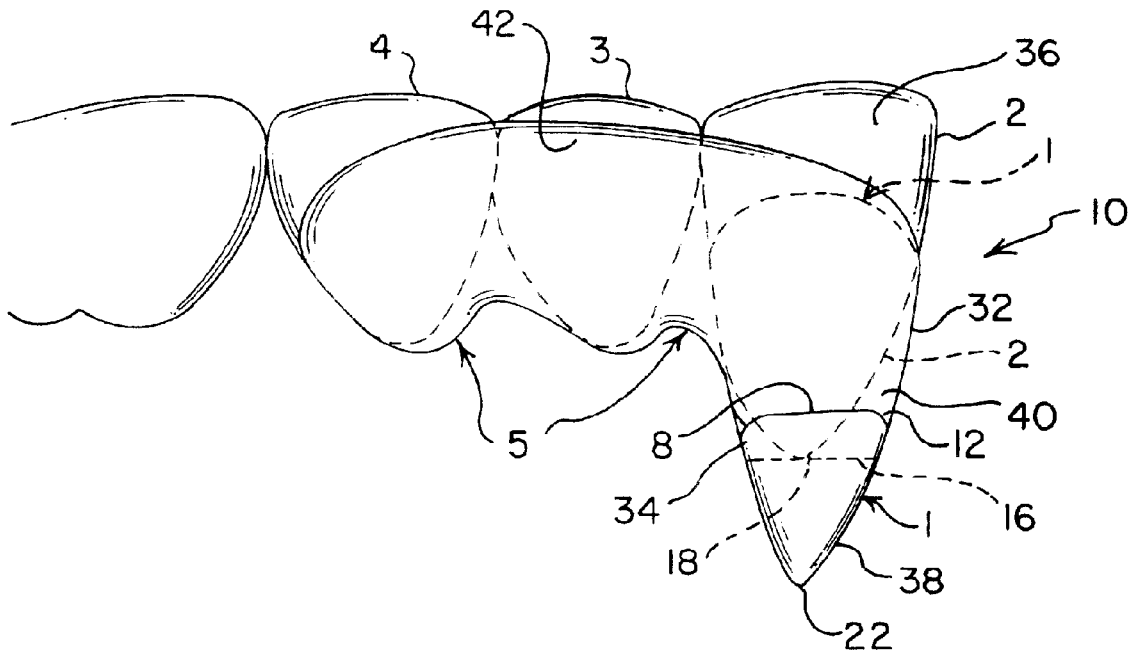

REEXAMINATION CERTIFICATE ISSUED UNDER 35 U.S.C. 307

NO AMENDMENTS HAVE BEEN MADE TO THE PATENT

AS A RESULT OF REEXAMINATION, IT HAS BEEN DETERMINED THAT:

The patentability of claims 1–15 is confirmed.

\* \* \* \* \*